(12) United States Patent
Alheidt et al.

(10) Patent No.: US 11,083,848 B2
(45) Date of Patent: Aug. 10, 2021

(54) FLUSH SYRINGE HAVING ANTI-REFLUX FEATURES

(71) Applicant: Becton, Dickinson and Company, Franklin Lakes, NJ (US)

(72) Inventors: Thomas A. Alheidt, Stockholm, NJ (US); Tracy Ray Hottovy, Wilson, NC (US); Dustin Drake, Columbus, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 451 days.

(21) Appl. No.: 16/181,713

(22) Filed: Nov. 6, 2018

(65) Prior Publication Data

US 2019/0070365 A1  Mar. 7, 2019

Related U.S. Application Data

(60) Continuation of application No. 14/722,488, filed on May 27, 2015, now Pat. No. 10,149,941, which is a
(Continued)

(51) Int. Cl.
 *A61M 5/31* (2006.01)
 *A61M 5/315* (2006.01)
 *A61M 5/50* (2006.01)

(52) U.S. Cl.
 CPC ...... *A61M 5/3146* (2013.01); *A61M 5/31501* (2013.01); *A61M 5/5013* (2013.01);
(Continued)

(58) Field of Classification Search
 CPC ............ A61M 5/3146; A61M 5/31501; A61M 5/5013; A61M 5/502; A61M 2005/3104
(Continued)

(56) References Cited

U.S. PATENT DOCUMENTS 3,050,059 A   8/1962  Wall et al.
3,478,937 A   11/1969  Solowey
(Continued)

FOREIGN PATENT DOCUMENTS

EP   1106194 A1   6/2001
WO   95/01811 A1   1/1995
(Continued)

OTHER PUBLICATIONS

Final Office Action in U.S. Appl. No. 10/530,817, dated Apr. 22, 2008, 9 pages.
(Continued)

*Primary Examiner* — Phillip A Gray
(74) *Attorney, Agent, or Firm* — Servilla Whitney LLC

(57) ABSTRACT

An I.V. flush syringe assembly includes a barrel having an inside surface defining a chamber for retaining fluid, an open proximal end and a distal end with a passageway therethrough in fluid communication with the chamber. An elongate plunger having a proximal end, a distal end and a flexible stopper is slidably positioned in fluid-tight engagement with the inside surface of the barrel for drawing fluid into and out of the chamber by movement of the stopper relative to the barrel. The barrel includes anti-reflux structure for holding said stopper in a partially deflected position after fluid has been delivered from the chamber and the stopper is being force against the distal end of the chamber.

9 Claims, 9 Drawing Sheets

Related U.S. Application Data division of application No. 10/530,817, filed as application No. PCT/US03/29918 on Sep. 23, 2003, now Pat. No. 9,072,844.

(60) Provisional application No. 60/418,053, filed on Oct. 11, 2002.

(52) U.S. Cl.
CPC ..... *A61M 5/502* (2013.01); *A61M 2005/3104* (2013.01); *A61M 2005/31516* (2013.01); *A61M 2005/31523* (2013.01)

(58) Field of Classification Search
USPC .......................................................... 604/187
See application file for complete search history.

(56) References Cited

U.S. PATENT DOCUMENTS

| | | | |
|---|---|---|---|
| 4,057,052 A | 11/1977 | Kaufman et al. | |
| 4,367,738 A | 1/1983 | Legendre et al. | |
| 4,391,272 A | 7/1983 | Staempfli | |
| 4,493,703 A | 1/1985 | Butterfield | |
| 4,731,068 A | 3/1988 | Hesse | |
| 4,781,684 A | 11/1988 | Trenner | |
| 4,820,272 A | 4/1989 | Palmer | |
| 4,832,693 A | 5/1989 | Gloyer et al. | |
| 4,950,240 A | 8/1990 | Greenwood et al. | |
| 4,973,310 A | 11/1990 | Kosinski | |
| 5,021,047 A * | 6/1991 | Movern | A61M 5/5013 604/110 |
| 5,037,393 A | 8/1991 | Ellgass | |
| 5,106,372 A | 4/1992 | Ranford | |
| 5,120,314 A | 6/1992 | Greenwood | |
| 5,222,945 A | 6/1993 | Basnight | |
| 5,354,284 A * | 10/1994 | Haber | A61M 5/19 604/191 |
| 5,373,971 A | 12/1994 | Laffy et al. | |
| 5,395,339 A | 3/1995 | Talonn et al. | |
| 5,496,285 A | 3/1996 | Schumacher et al. | |
| 5,522,804 A | 6/1996 | Lynn | |
| 5,549,569 A | 8/1996 | Lynn | |
| 5,593,387 A | 1/1997 | Rupp | |
| 5,743,886 A | 4/1998 | Lynn et al. | |
| 5,807,374 A | 9/1998 | Caizza et al. | |
| 5,902,271 A | 5/1999 | Jentzen | |
| 6,171,287 B1 | 1/2001 | Lynn et al. | |
| 6,228,065 B1 | 5/2001 | Lynn | |
| 6,361,524 B1 | 3/2002 | Odell et al. | |
| 2004/0010235 A1 | 1/2004 | Weilbacher et al. | |

FOREIGN PATENT DOCUMENTS

| | | |
|---|---|---|
| WO | 95/21639 A1 | 8/1995 |
| WO | 99/52578 A2 | 10/1999 |

OTHER PUBLICATIONS

Final Office Action in U.S. Appl. No. 10/530,817, dated Feb. 18, 2010, 9 pages.
Final Office Action in U.S. Appl. No. 10/530,817, dated Jun. 19, 2009, 9 pages.
Final Office Action in U.S. Appl. No. 10/530,817, dated Nov. 22, 2010, 9 pages.
Non-Final Office Action in U.S. Appl. No. 10/530,817, dated Aug. 9, 2007, 8 pages.
Non-Final Office Action in U.S. Appl. No. 10/530,817, dated Jan. 22, 2009, 7 pages.
Non-Final Office Action in U.S. Appl. No. 10/530,817, dated Jul. 19, 2010, 11 pages.
Non-Final Office Action in U.S. Appl. No. 10/530,817, dated Nov. 28, 2006, 13 pages.
Non-Final Office Action in U.S. Appl. No. 10/530,817, dated Sep. 30, 2009, 7 pages.
PCT International Preliminary Examination Report, in PCT/US03/29918, dated Aug. 18, 2004, 2 pages.
PCT International Search Report in PCT/US03/29918, dated Mar. 19, 2004, 4 pages.

\* cited by examiner

FLUSH SYRINGE HAVING ANTI-REFLUX FEATURES

CROSS REFERENCE TO RELATED APPLICATIONS

This is a continuation of pending U.S. application Ser. No. 14/722,488, filed May 27, 2015, which is a divisional of pending U.S. application Ser. No. 10/530,817, filed Apr. 8, 2005, and issued on Jul. 7, 2015, as U.S. Pat. No. 9,072,844, which is the National Phase entry of International Application No. PCT/US03/29918, filed Sep. 23, 2003, which claims priority from U.S. Provisional Application No. 60/418,053, filed Oct. 11, 2002.

BACKGROUND OF THE INVENTION

The present invention relates to syringe assemblies and particularly to syringe assemblies for use in I.V. flush procedures.

An I.V. catheter is a commonly used therapeutic device. Many patients, in accordance with their therapy, have an I.V. catheter connected to a vein ready for use in various procedures or in fluid communication with an I.V. system for infusing liquids and medication. Many I.V. sets have I.V. ports which are in fluid communication with a catheter and allow access for the purpose of injecting medication into the patient, and for use in flushing techniques to maintain catheter integrity. Healthcare facilities have flushing protocols which depend on the amount of time the catheter will remain in the patient and the type of catheter being used. For example, a peripherally inserted central catheter (PICC) is a long flexible catheter, which is typically inserted into the central venous system (optimally with the tip terminating in the superior vena cava) via the superficial veins of the antecubital fossa. PICC lines are designed for use when intermediate or long-term therapy is prescribed.

These catheter lines must be periodically flushed with saline flush solution and/or heparin lock flush solution depending on the protocol. Among other things, flushing saline solution removes blood from the catheter and heparin helps prevent the formation of future blood clots. The most common I.V. ports are covered by pierceable septums or pre-slit septums and are known in the art and sometimes referred to as "PRN" from the Latin pro re rata meaning "as the need arises". The septum is preferably made of rubber or another elastomeric material which permits insertion of a sharp needle cannula in order to infuse fluids into or to withdraw fluids from the catheter. Upon withdrawal of the needle cannula the septum seals itself. Ports having pre-slit septums are used with blunt cannula. Typically, the blunt cannula is attached to a syringe and the syringe is moved to place a gentle pressure on the pre-slit septum which is forced open by the blunt cannula to establish fluid communication. Also, some I.V. sets have access valves which are responsive to the frusto-conically shaped tip of a syringe barrel for allowing fluid communication between the interior of the syringe and the catheter.

Catheters are flushed using syringe assemblies filled with various fluids. In some cases, different fluids are injected sequentially in accordance with the protocol. For example, a saline solution followed by an anticoagulant such as heparin. The size of the syringe used to flush I.V. lines varies by various factors including the size and length of the catheter. Typically syringes of 1 ml, 3 ml, 5 ml and 10 ml volume are used.

It is important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve slowly withdrawing the syringe and cannula from the I.V. port while still applying pressure to the syringe plunger rod during the flush procedure. When using a syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size drawing liquid from the catheter into the syringe barrel. This is undesirable, since it can cause blood to enter the catheter at the catheter distal end (reflux).

Therefore there is a need for simple, straight forward easy-to-manufacture syringe assemblies which reduce or eliminate reflux of blood into the catheter during and after the flushing procedure has occurred without changing flush protocols and procedures.

SUMMARY OF THE INVENTION

The present invention is directed to a syringe having a compressible stopper. The stopper is held in position at the distal end of the barrel at the completion of the flush procedure. The stopper is held in a compressed form, by structure resisting its expansion. Since expansion of the stopper is substantially prevented at the completion of the flush procedure, reflux of blood into the catheter is minimized and/or eliminated.

An I.V. flush syringe assembly includes a barrel having an inside surface defining a chamber for retaining fluid, an open proximal end and a distal end including a distal wall with an elongate tip extending distally therefrom having a passageway therethrough in fluid communication with the chamber. A plunger including an elongate body portion having a proximal end, a distal end with a flexible stopper slidably positioned in fluid-tight engagement with the inside surface of the barrel for drawing fluid into and driving fluid out of the chamber by movement of the stopper relative to the barrel. The elongate body portion of the plunger extends outwardly from the open proximal end of the barrel. The I.V. flush syringe includes anti-reflux means for holding the stopper in a partially deflected position when fluid has been delivered from the chamber and the stopper is in contact with the distal wall of the barrel. Such anti-reflux means provide structure on the stopper and/or barrel to hold the stopper in a partially deflected position to minimize or eliminate reflux by preventing the stopper from moving proximally and drawing blood into the catheter.

The anti-reflux structure can include the stopper having an outwardly projecting rib and the inside surface of the barrel having a recess for receiving the rib when the stopper is in contact with and partially compressed against the distal wall of the barrel. The projection on the stopper may include one or more annular ribs and the recess in the barrel may include one or more annular grooves for accepting the ribs.

The anti-reflux structure may also include a contact area on the inside surface of the barrel at the distal end of the barrel. The contact area has a higher coefficient of friction than the inside surface of the barrel which is outside of the contact area. The contact area is for engaging the stopper when the stopper is in contact and compressed against the distal wall of the barrel. The contact area may include a plurality of annular deformations. These deformations may be projections on the inside surface of the barrel.

A method of flushing a catheter of the present invention comprises the steps of providing a syringe assembly including a barrel having an inside surface defining a chamber for retaining fluid, an open proximal end and a distal end including a distal wall with an elongate tip extending distally therefrom having a passageway therethrough in fluid communication with the chamber, a plunger including an elongate body portion having a proximal end, a distal end and a flexible stopper slidably positioned in fluid-tight engagement with the inside surface of the barrel for drawing fluid into and driving fluid out of the chamber by movement of the stopper relative to the barrel, the elongate body portion of the plunger extending outwardly from the open proximal end of the barrel, a quantity of flush solution in the chamber, and anti-reflux means for holding the stopper in a partially deflected position when the flush solution has been delivered from said chamber and the stopper is in contact with the distal wall. The method further includes providing a catheter having a proximal end, a distal end and a passageway therethrough and a housing having a hollow interior connected to the catheter and in fluid communication with the passageway, the housing having an access valve for allowing fluid communication with the hollow interior. The method further includes the additional steps of: placing the distal end of the catheter in a blood vessel; engaging the elongate tip of the barrel with the access valve so that the passageway of the syringe barrel is in fluid communication with the hollow interior of the housing; applying force to the plunger to move the stopper in a distal direction with respect to the barrel so that the flush solution in the chamber flows through the passageway into the hollow chamber of the housing and through the passageway of the catheter; and continue applying force to the plunger until the stopper contacts and presses against the distal wall of the barrel and is held in a partially deflected position by anti-reflux means.

An alternate method includes the step of attaching a needle assembly to the elongate tip of the barrel. The needle assembly includes a cannula having a proximal end, a distal end and a lumen therethrough and a hub having an open proximal end containing a cavity and a distal end attached to the proximal end of the cannula so that the lumen is in fluid communication with the cavity. The attachment of the needle assembly to the barrel is through frictional engagement between the cavity in the hub and the elongate tip. This alternative method is used with a catheter having a proximal end, a distal end and a passageway therethrough and a housing having a hollow interior connected to the catheter and in fluid communication with the passageway of the catheter. The housing further includes a septum for allowing fluid communication with the hollow interior. Fluid communication is established by forcing the distal end of the cannula through the septum so that the lumen of the cannula is in fluid communication with the hollow interior of the housing. Also, the cannula may be permanently attached to the needle tip without the use of a hub.

DETAILED DESCRIPTION

Figure 1:
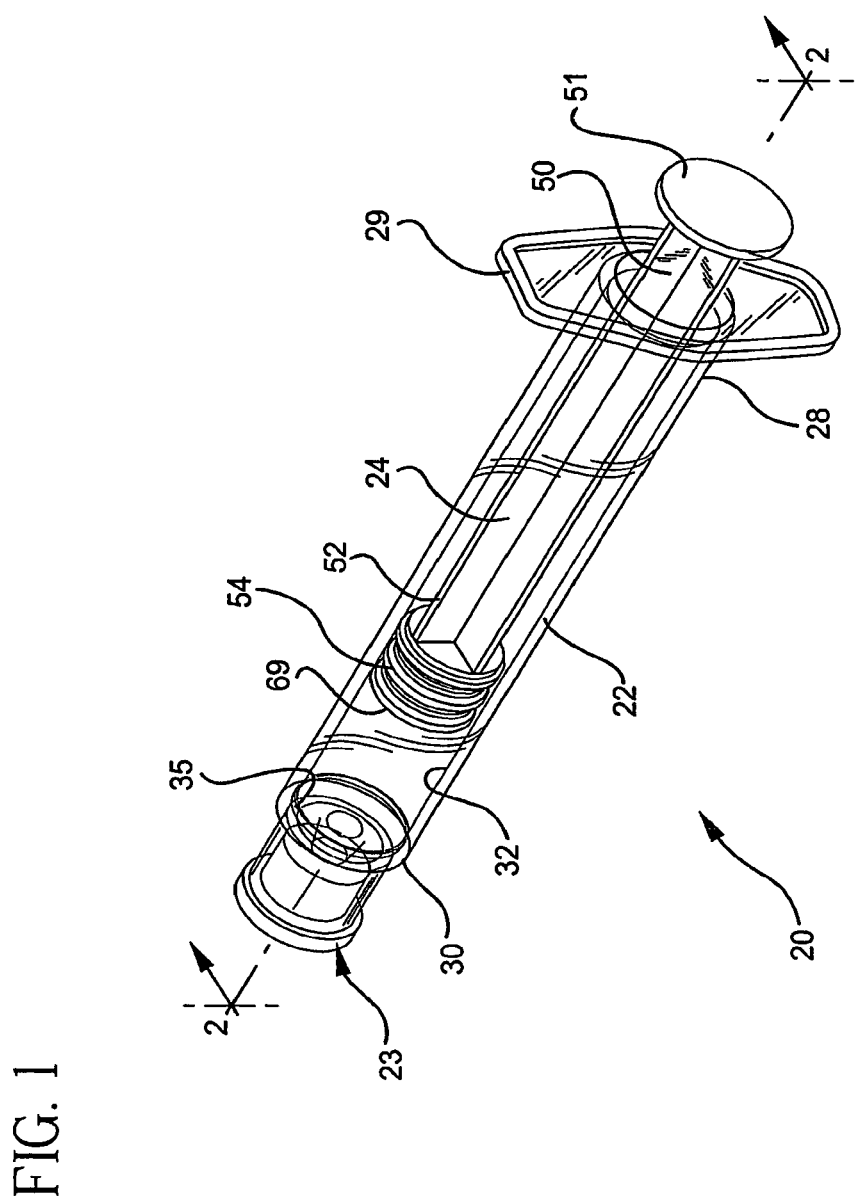
FIG. 1 is a perspective view of a syringe assembly according to one embodiment of the invention.
Figure 2:
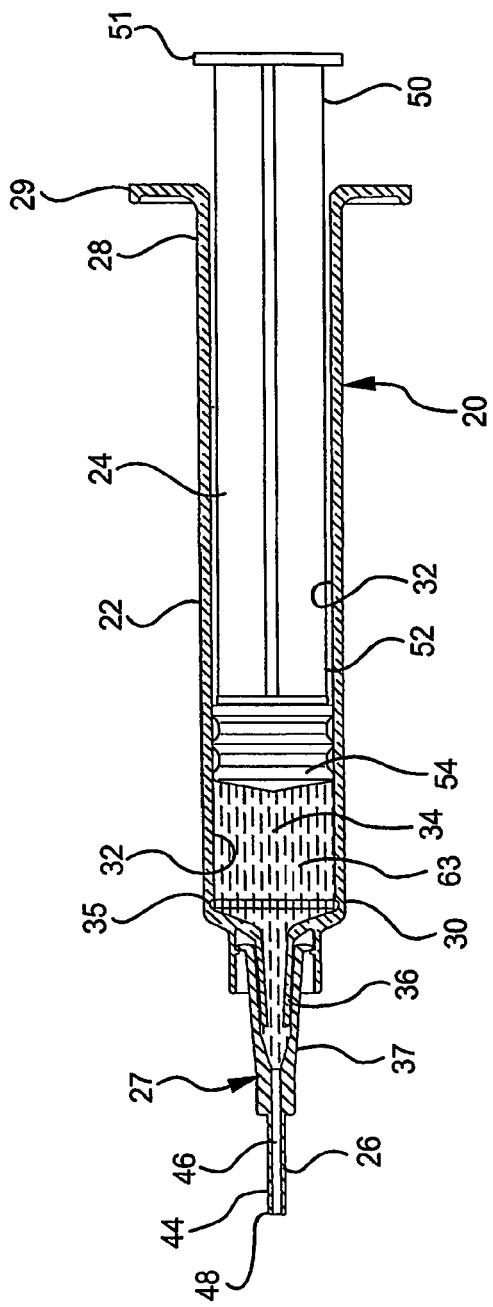
FIG. 2 is a partially cross-sectioned side-elevational view of the syringe of FIG. 1 with a needle assembly attached.
Figure 3:
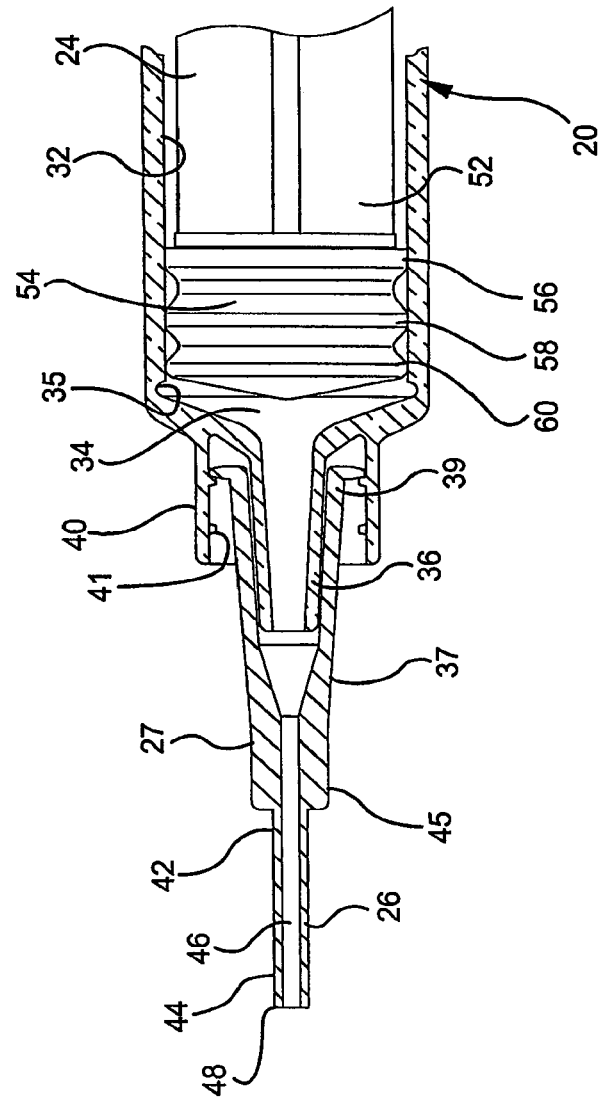
FIG. 3 is an enlarged partial cross-sectional side elevation view of the distal end of the syringe assembly of FIG. 2.
Figure 4:
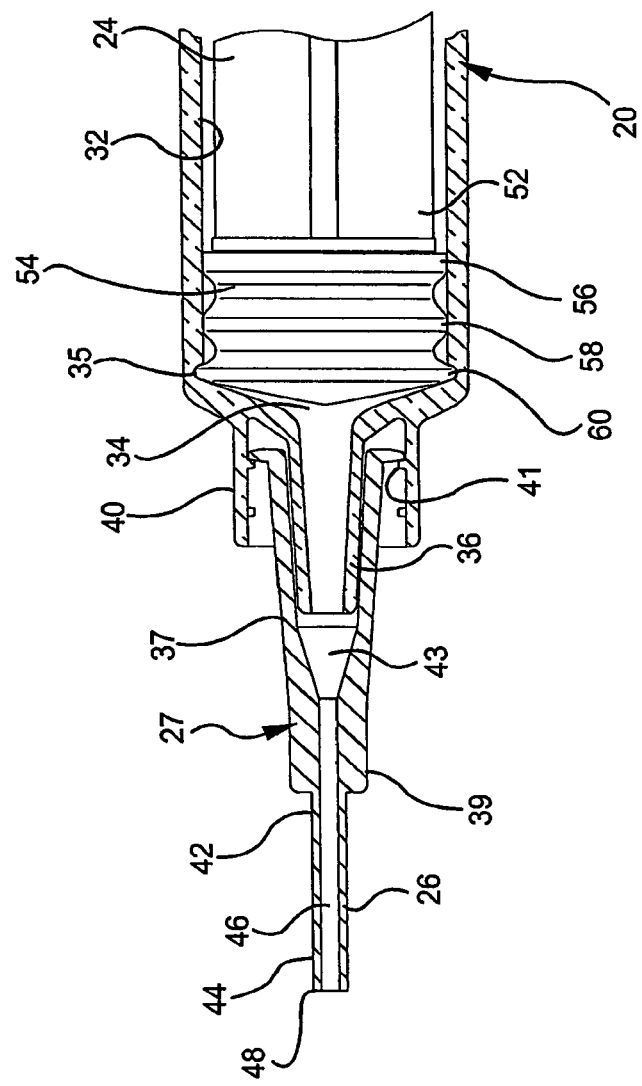
FIG. 4 is an enlarged partial cross-sectional side-elevational view of the distal end of the syringe assembly of FIG. 2 with the stopper positioned in its distal-most position after flush solution has been delivered.

FIGS. 1-4 show a syringe 20 according to the present invention generally comprising a barrel 22, a plunger 24. Barrel 22 has a generally elongate body including an open proximal end 28 having finger grips 29, a distal end 30 and an inside surface 32 defining a fluid chamber 34. Inside surface 32 includes a generally annular recess 35 towards distal end 30. Distal end 30 further includes a tip 36 having a passageway 38 in fluid communication with the chamber 34. The distal end of barrel 22 preferably, but does not necessarily include a locking luer type collar 40 concentrically surrounding tip 36. The inside surface of the collar includes at least one thread 41. A cannula 26 includes a proximal end 42, a distal end 44 and a lumen 46 therethrough. The distal end may include a sharp tip or a blunt tip 48 as shown. The cannula may be connected directly to the tip of the syringe barrel to establish fluid communication between the lumen and the chamber. Also, the cannula may be part of a needle assembly 27 including a hub 37 having an open proximal end 39 containing a cavity 43 and a distal end 45 attached to the proximal end of the cannula so that the lumen of the cannula is in fluid communication with the cavity. The cavity of the hub can be removably frictionally engaged to the tip of the barrel as illustrated in FIGS. 2-4.

Plunger 24 includes a proximal end 50 having a flange 51 and a distal end 52. A flexible stopper 54 is disposed on the distal end of plunger 24. Stopper 54 includes at least one annular rib and in this embodiment includes a proximal rib 56, a middle rib 58 and a distal rib 60. The stopper comprises any flexible resilient material suitable for providing sealing characteristics while under compression. For example, the stopper may be made of thermoplastic elastomers, natural rubber, synthetic rubber and the like.

In operation, the syringe 20 is connected to a hypodermic needle assembly and filled with flush solution using known methods. The flush solution may be any solution intended for flushing. It is preferred that the flush solution be selected from the group consisting of saline flush solution and heparin lock flush solution. These solutions are known in the art and readily available. An example of a saline flush solution is 0.9% Sodium Chloride USP. An example of a heparin lock flush solution is 0.9% sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial containing flush solution and the flush solution is drawn into the syringe barrel by pulling plunger rod flange 51 in the proximal direction while holding barrel 22, to draw fluid through the needle cannula into the fluid chamber 34.

Alternatively, the syringe may be filled with flush solution during the manufacturing of the syringe via a sterile filling method. Such prefilled syringes may be supplied with a tip cap, such as tip cap 23 releasably connected to tip 36 sealing passageway 38. It is preferred that the tip cap is formed of material selected from the group of thermoplastic materials and elastomeric materials such as natural and synthetic rubber and thermoplastic elastomers.

Figure 5:
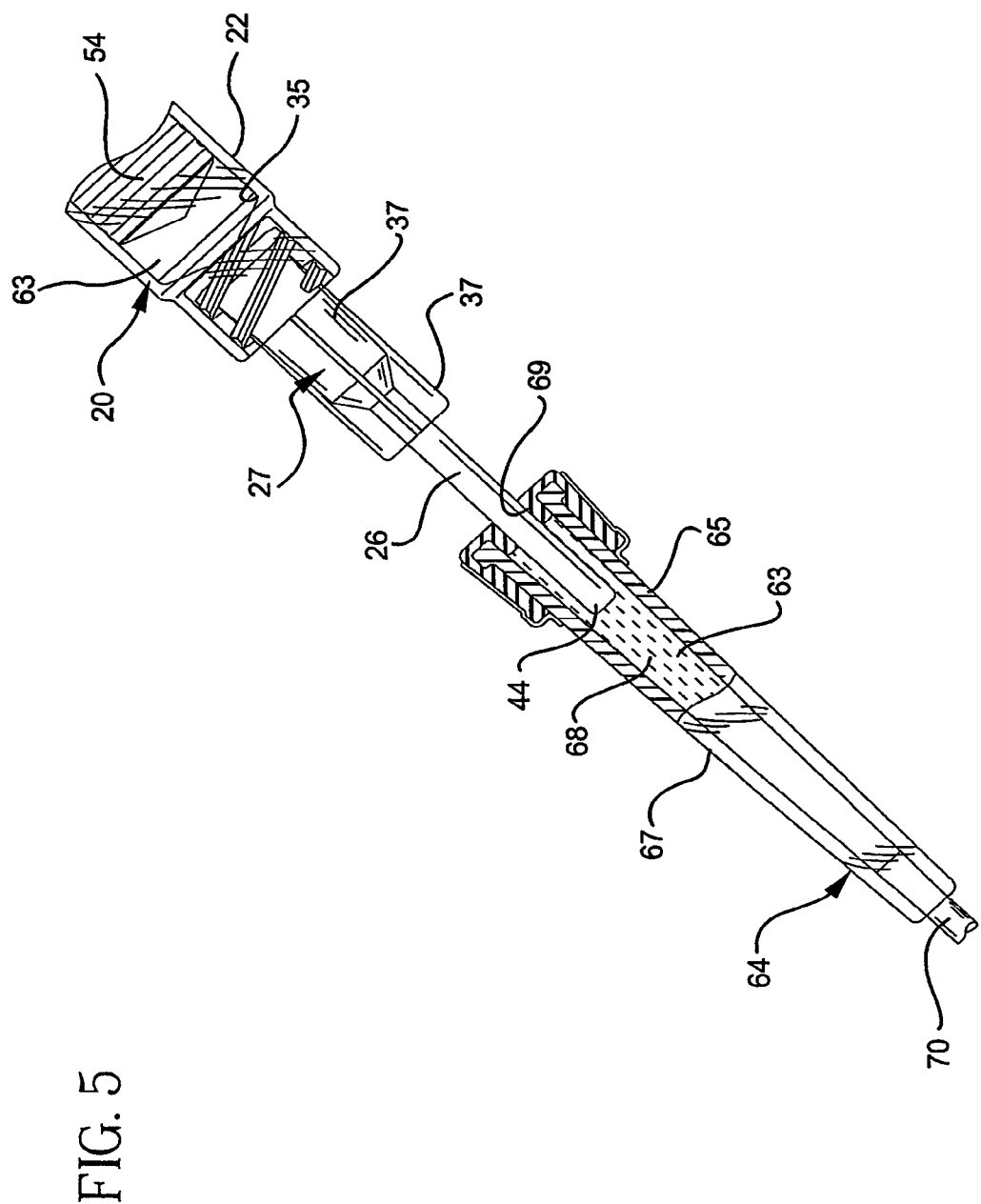
FIG. 5 is a side-elevational view illustrating the syringe assembly in use with a catheter injection site.
Figure 6:
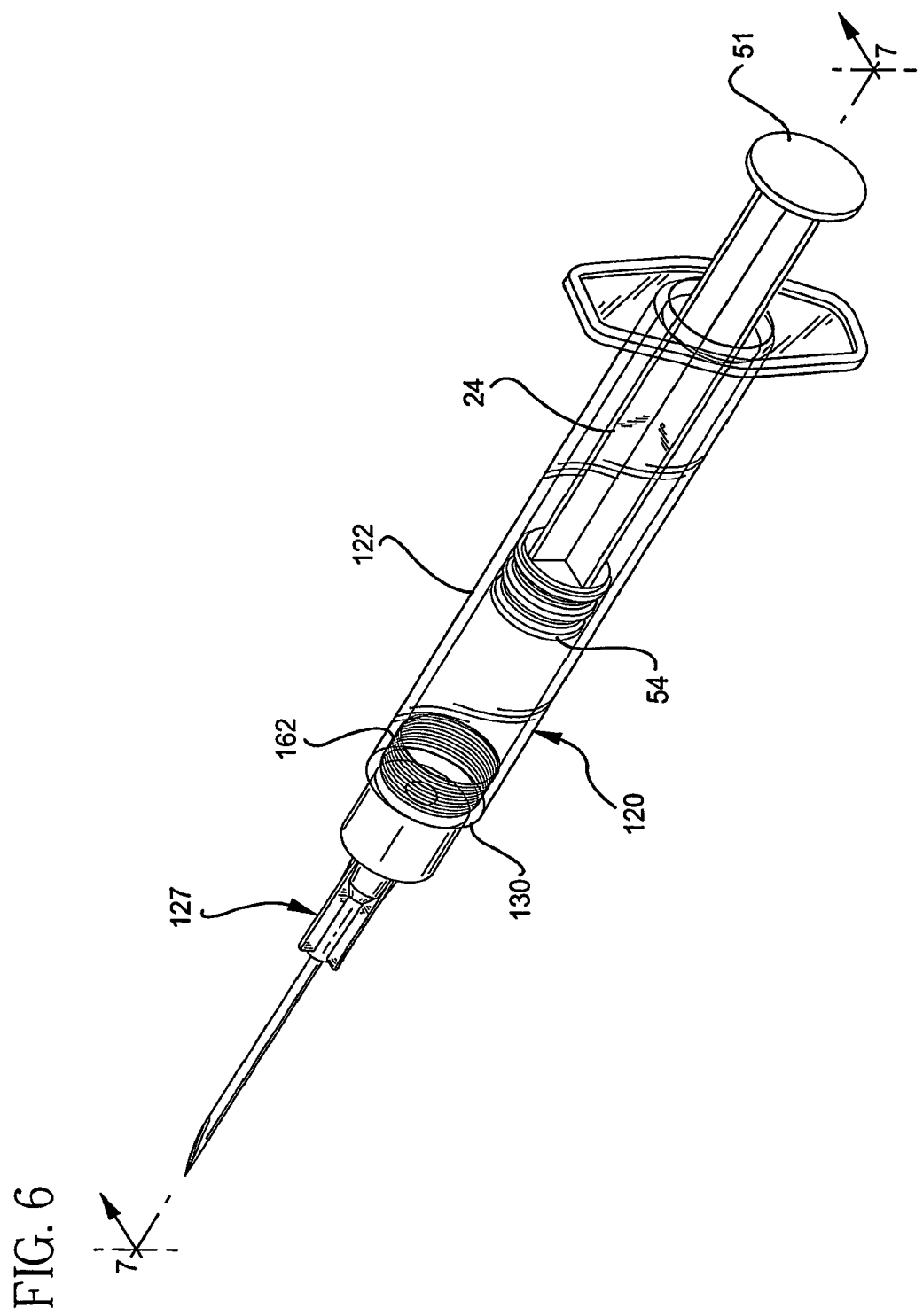
FIG. 6 is a perspective view of a syringe assembly according to another embodiment of the invention.
Figure 7:
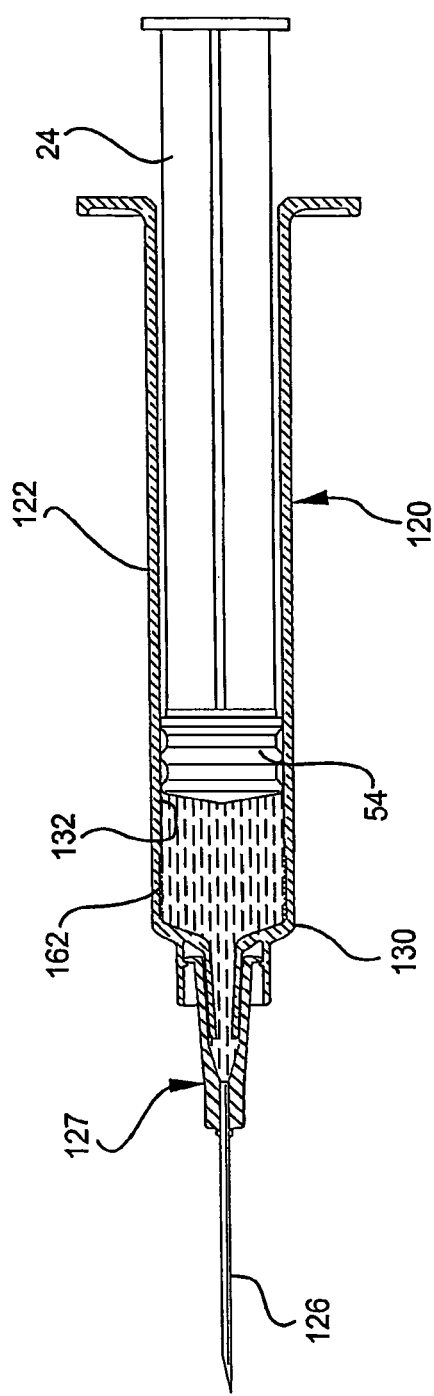
FIG. 7 is a partially cross-sectioned side-elevational view of the syringe assembly of FIG. 6.
Figure 8:
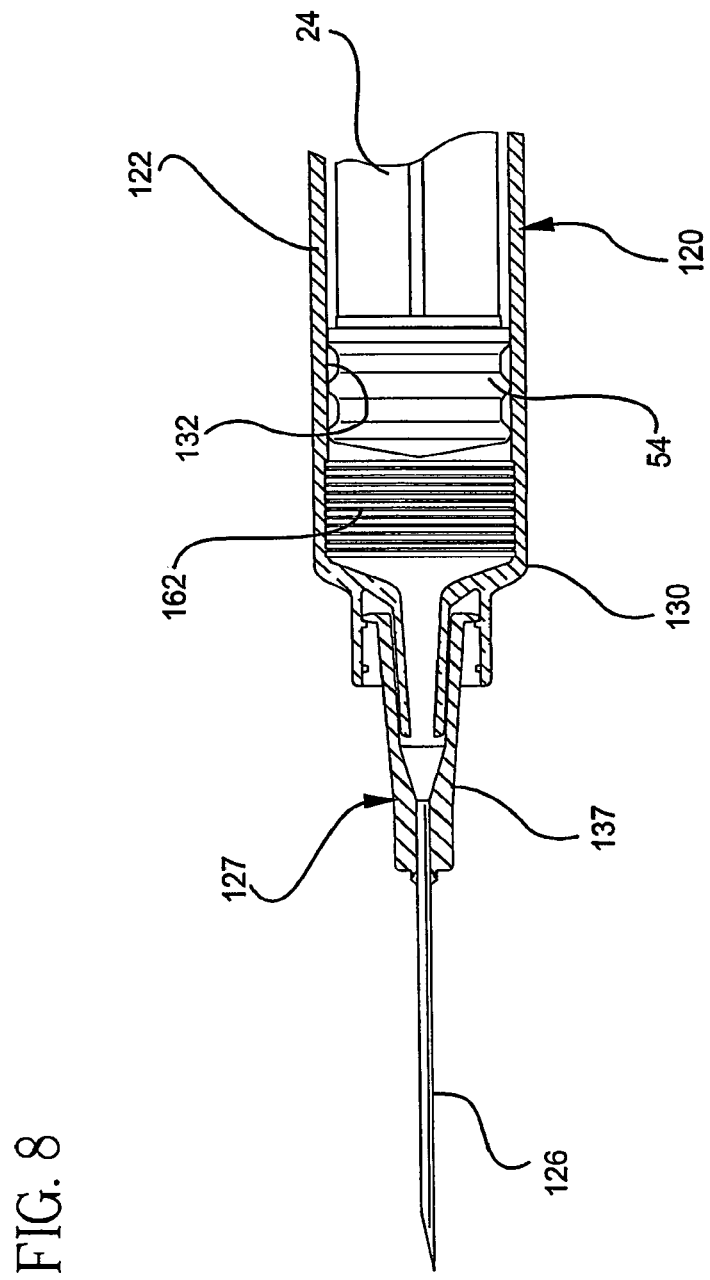
FIG. 8 is an enlarged cross-sectional side elevation view of the distal end of the syringe assembly of FIG. 7.
Figure 9:
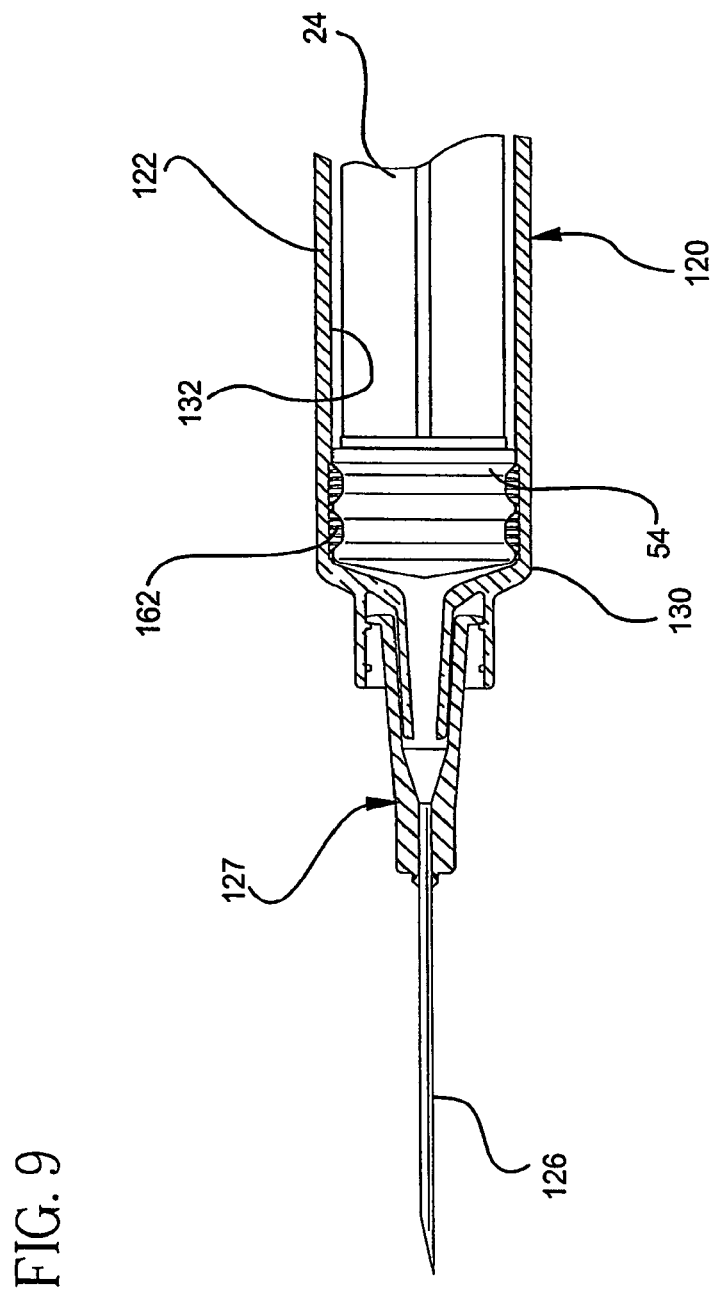
FIG. 9 is an enlarged cross-sectional side elevational view of the distal end of the syringe assembly of FIG. 7 with the stopper positioned in its distal-most position after flush solution has been delivered.

The syringe is now ready for use in flushing a catheter of an I.V. set. I.V. sets can be very complicated and may include multiple injection ports, a valve and/or other components. For the purpose of illustrating the present invention a simplified I.V. set 64 is illustrated in FIG. 5. I.V. set 64 comprises an I.V. site 65 which includes a housing 67 having a hollow interior 68 and a septum 69 at its proximal end. A catheter 70 having a conduit therethrough extends from the distal end of the housing. For this I.V. set, septum 69 is pre-slit for use with blunt cannula. The I.V. site may have a pierceable septum or a valve having structure for accepting the syringe barrel tip and being activated by the insertion of the tip to establish fluid communication with the catheter, such as the valve taught in U.S. Pat. No. 6,171,287.

Blunt tip 48 of cannula 26 may be inserted through pre-split septum 69 of I.V. set 64. Alternatively, a sharp tip of a needle cannula may be used to pierce a septum that it not pre-split, or the tip of the barrel may be engaged with a valve in the IV site. This establishes fluid communication between the interior 68 of the I.V. set and the chamber of the syringe barrel. The syringe barrel 22 is preferably held via finger grips 29. Pressure is then applied to flange 51 of the plunger, for example by a thumb, in the distal direction. This moves the plunger 24 having the stopper 54 on its distal end, forcing the liquid such as flush solution 35 in the chamber 34 out of the chamber, through cannula 26 and into interior 68 of the I.V. set and then through catheter 70.

Referring to FIG. 4, the position of the plunger and stopper at the completion of the flush procedure is shown. As shown, the flange 51 does not contact the proximal end of the barrel at the completion of the flush procedure. Stopper 54 is now compressed. Distal rib 60 of the stopper is received within recess 35 of the barrel. Distal rib 60 fits within the recess 35 preferably via a friction fit or an interference fit. Thus, the stopper 54 is held in position at the distal end of the barrel 22. This, in turn, holds the plunger 24 within the barrel. Therefore, reflux of liquid, including blood, into the catheter is prevented or minimized since the stopper is held in a compressed form and will not withdraw into the proximal direction.

It is within the purview of the present invention to include additional recesses at the distal end of the barrel to receive the middle rib and the proximal rib. In such an embodiment, the recesses would be spaced apart in order to receive the ribs when the stopper is in a compressed form, typical at the end of the flush procedure.

FIGS. 6-9 shown another embodiment of the invention where like elements are similarly numbered. In this embodiment of the invention, syringe assembly 120 includes plunger 24 and barrel 122. A needle assembly 127 includes cannula 126 having a sharp distal end and hub 137 attached to distal end 130 of the barrel. Inside surface 132 of syringe barrel 122 includes a contact area 162. The contact area may be, for example, one or more discontinuities, and/or a roughened portion of the inside surface. In operation, after the flush procedure has occurred, the stopper 54 is compressed at the distal end of the barrel within contact area 162 of the barrel. The contact area restrains the stopper from moving in the proximal direction. Therefore, stopper 54 is frictionally restrained by the contact area 162, holding stopper 54 and plunger 24 within the barrel. The force required to overcome the friction between the stopper 54 and contact area 162 is more than the force required to overcome the friction between the stopper and the inside surface the barrel outside of the contact area. The force between the stopper and the contact area is sufficient to hold the stopper in a partially compressed state after the stopper contacts the distal end of the chamber. Thus, the stopper 54 is restrained from expanding out of its compressed form thereby preventing or minimizing reflux.

Although the invention herein has been described with reference to particular embodiments it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. An I.V. flush syringe assembly comprising:
    a barrel having an inside surface defining a chamber for retaining fluid, an open proximal end and a distal end including a distal wall with an elongate tip extending distally therefrom having a passageway therethrough in fluid communication with said chamber, said inside surface having distal annular recess at the distal end;
    a plunger including an elongate body portion having a proximal end, a distal end and a flexible stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel and said flexible stopper including a distal annular rib, a middle annular rib and a proximal annular rib wherein said distal annular rib is configured to be received within said annular recess at said distal end of said barrel via a friction fit or an interference fit upon completion of a flush procedure, thereby holding said stopper in compressed form and preventing withdrawal of said stopper in a proximal direction.

2. The I.V. flush syringe assembly of claim 1, wherein the inside surface of the barrel further comprises a middle annular recess configured to receive the middle annular rib upon completion of the flush procedure when the stopper is held in compressed form.

3. The I.V. flush syringe assembly of claim 2, wherein the inside surface of the barrel further comprises a proximal annular recess configured to receive the proximal annular rib upon completion of the flush procedure when the stopper is held in compressed form.

4. The I.V. flush syringe assembly of claim 1, further comprising a flush solution in the chamber and a tip cap releasably connected to the tip to seal the passageway.

5. The I.V. flush syringe assembly of claim 4, wherein the flush solution is a saline flush solution or a heparin lock flush solution.

6. The I.V. flush syringe assembly of claim 1, wherein the flexible stopper is made of thermoplastic elastomers, natural rubber, or synthetic rubber.

7. A method of preventing or minimizing reflux after flushing a catheter comprising the steps of:

(a) providing an I.V. flush syringe assembly according to claim 1 having a quantity of flush solution in the chamber;

(b) providing a catheter having a proximal end, a distal end and a passageway therethrough and a housing having a hollow interior connected to said catheter and in fluid communication with said passageway of said catheter;

(c) placing said distal end of said catheter in a blood vessel;

(d) establishing fluid communication between said passageway of said barrel and said hollow interior of said housing;

(e) applying force to said plunger to move said stopper in a distal direction with respect to said barrel so that said flush solution in said chamber flows through said passageway of said barrel into said hollow interior of said housing and through said passageway of said catheter;

(f) continuing to apply force to the plunger until said stopper contacts, and is compressed against, said distal wall of said barrel, such that the distal annular rib of the stopper is received within the distal annular recess and held in compressed form, thereby preventing withdrawal of the stopper in a proximal direction.

8. The method of claim 7, wherein the inside surface of the barrel further comprises a middle annular recess and the middle annular rib is received in the middle annular recess when the stopper is held in compressed form.

9. The method of claim 8, wherein the inside surface of the barrel further comprises a proximal annular recess and the proximal annular rib is received in the proximal annular recess when the stopper is held in compressed form.

* * * * *